(12) United States Patent
Kawanishi

(10) Patent No.: US 10,194,881 B2
(45) Date of Patent: Feb. 5, 2019

(54) RADIOGRAPHIC IMAGE PROCESSING DEVICE, METHOD, AND RECORDING MEDIUM

(71) Applicant: FUJIFILM Corporation, Tokyo (JP)

(72) Inventor: Masanori Kawanishi, Kanagawa-ken (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 9 days.

(21) Appl. No.: 15/242,741

(22) Filed: Aug. 22, 2016

(65) Prior Publication Data

US 2016/0354052 A1    Dec. 8, 2016

Related U.S. Application Data

(63) Continuation of application No. PCT/JP2015/001104, filed on Mar. 3, 2015.

(30) Foreign Application Priority Data

Mar. 5, 2014   (JP) .................................. 2014-042495

(51) Int. Cl.
*A61B 6/00*     (2006.01)
*A61B 5/107*    (2006.01)

(52) U.S. Cl.
CPC ............ *A61B 6/5282* (2013.01); *A61B 6/461* (2013.01); *A61B 6/50* (2013.01); *A61B 6/5258* (2013.01);

(Continued)

(58) Field of Classification Search
CPC ... A61B 5/02007; A61B 5/0538; A61B 5/064; A61B 5/6853; A61B 6/504; A61B 6/541;
(Continued)

(56) References Cited

U.S. PATENT DOCUMENTS 3,949,229 A * 4/1976 Albert .................... A61B 6/145
378/98.6
5,878,108 A * 3/1999 Baba .................... A61B 6/5282
378/7

(Continued)

FOREIGN PATENT DOCUMENTS

JP    2002-133410 A    5/2002
JP    2008-220414 A    9/2008
(Continued)

OTHER PUBLICATIONS

Communication dated Dec. 6, 2016, issued by the Intellectual Property Office of Japan in corresponding application No. 2014-042495.

(Continued)

*Primary Examiner* — Aklilu Woldemariam
(74) *Attorney, Agent, or Firm* — Sughrue Mion, PLLC

(57) ABSTRACT

A radiographic image which is captured by irradiating a subject with radiation is acquired. A body thickness information acquisition unit acquires body thickness information of a subject. The radiographic image may be analyzed to acquire the body thickness information. A noise removal unit removes quantum noise included in the radiographic image on the basis of the body thickness information, using a filtering process using, for example, a smoothing filter.

10 Claims, 6 Drawing Sheets

(52) U.S. Cl.
CPC ............... *A61B 5/1075* (2013.01); *A61B 6/00* (2013.01); *A61B 6/467* (2013.01); *A61B 6/544* (2013.01)

(58) Field of Classification Search
CPC ....... A61B 8/565; A61B 8/582; A61B 5/1075; A61B 2034/2065; A61B 2090/061; A61B 2090/3966; A61B 2090/3983; A61B 2502/00; A61B 6/5258; A61B 6/544; A61B 6/5282; A61B 6/461; A61B 6/467; A61B 6/50; A61B 6/42; A61B 6/4291; A61B 6/502; A61B 6/5205; A61B 6/5217; A61B 6/545; A61B 6/58; A61B 6/4208; A61B 6/4266; A61B 6/4283; A61B 6/548; A61B 6/56; A61B 6/506; A61B 6/025; A61B 6/06; A61B 6/08; A61B 6/4233; A61B 6/505; A61B 6/5241; A61B 6/542; A61B 6/547; A61B 6/5211; A61B 1/00087; A61B 6/145; A61B 6/4028; A61B 6/4464; A61B 6/525; A61B 2560/0214; A61B 2560/0266; A61B 6/52; G06T 2207/10116; G06T 7/0012; G06T 2207/30004; G06T 5/50; G06T 7/11; G06T 7/62; G06T 11/00; G06T 11/005; G06T 15/08; G06T 17/00; G06T 17/20; G06T 2207/10081; G06T 2207/20012; G06T 2207/20; G06T 2207/30068; G06T 5/008; G06T 2207/30101; G06T 5/40; G06T 11/006; G06T 11/008; G06T 11/60; G06T 19/006; H04N 5/32; H04N 5/3765; H04N 5/23241; G01T 1/026; G01T 1/2018; G01T 1/17; G01T 1/24
USPC ....... 382/100, 128, 132, 264, 129, 131, 154, 382/275
See application file for complete search history.

(56) References Cited

U.S. PATENT DOCUMENTS

| | | | | |
|---|---|---|---|---|
| 5,951,475 A | * | 9/1999 | Gueziec | G06T 3/0068 128/922 |
| 2002/0071600 A1 | * | 6/2002 | Yamada | G06T 5/004 382/132 |
| 2003/0072417 A1 | * | 4/2003 | Kaufhold | A61B 6/482 378/207 |
| 2005/0123184 A1 | * | 6/2005 | Avinash | H04N 5/217 382/132 |
| 2009/0060312 A1 | * | 3/2009 | Kitamura | G06T 5/50 382/132 |
| 2009/0285468 A1 | * | 11/2009 | Omi | G06T 5/50 382/132 |
| 2010/0142791 A1 | * | 6/2010 | Tsuji | G06T 5/50 382/132 |
| 2011/0002519 A1 | * | 1/2011 | Tomisaki | A61B 6/12 382/131 |
| 2011/0058725 A1 | * | 3/2011 | Markwardt | G06K 9/52 382/132 |
| 2011/0158386 A1 | * | 6/2011 | Payne | A61B 5/4872 378/54 |
| 2012/0130238 A1 | * | 5/2012 | Muraoka | A61B 6/4233 600/436 |
| 2013/0082184 A1 | * | 4/2013 | Nakatsugawa | A61B 6/4208 250/366 |
| 2013/0148782 A1 | * | 6/2013 | Tajima | A61B 6/542 378/62 |
| 2013/0163809 A1 | * | 6/2013 | Matsumoto | G01B 15/02 382/100 |
| 2014/0016749 A1 | * | 1/2014 | Oda | A61B 6/5258 378/62 |
| 2014/0021365 A1 | * | 1/2014 | Oda | G01T 1/17 250/395 |
| 2014/0023179 A1 | * | 1/2014 | Oda | A61B 6/542 378/62 |
| 2014/0110595 A1 | * | 4/2014 | Iwakiri | A61B 6/4233 250/394 |
| 2014/0205066 A1 | * | 7/2014 | Kitagawa | A61B 6/542 378/62 |
| 2014/0291541 A1 | * | 10/2014 | Watanabe | H04N 5/32 250/394 |
| 2016/0235384 A1 | * | 8/2016 | Enomoto | A61B 6/4291 |
| 2016/0350923 A1 | * | 12/2016 | Muraoka | G06T 7/20 |

FOREIGN PATENT DOCUMENTS

| | | |
|---|---|---|
| JP | 2008-246022 A | 10/2008 |
| JP | 2011-104103 A | 6/2011 |

OTHER PUBLICATIONS

Written Opinion of PCT/JP2015/001104 dated Jul. 7, 2015.
International Search Report for PCT/JP2015/001104 dated Jul. 7, 2015.

* cited by examiner

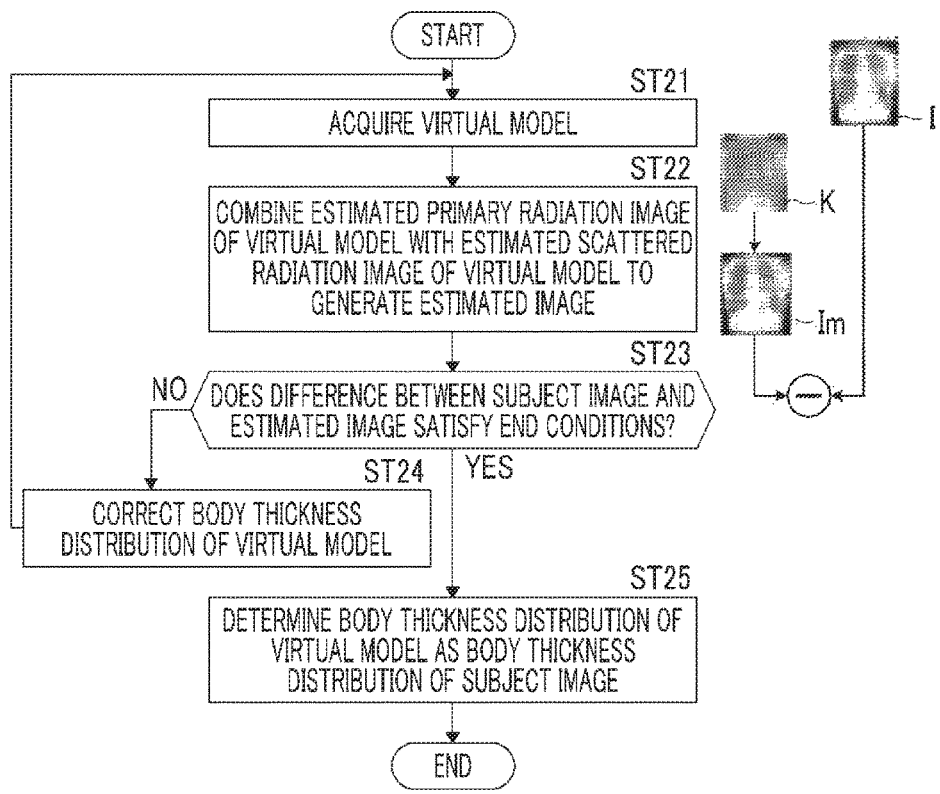
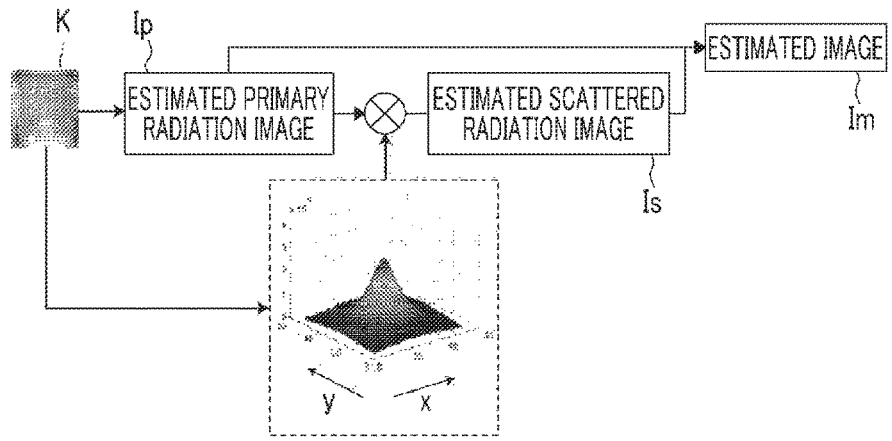

RADIOGRAPHIC IMAGE PROCESSING DEVICE, METHOD, AND RECORDING MEDIUM

CROSS REFERENCE TO RELATED APPLICATIONS

The present application is a Continuation of PCT International Application No. PCT/JP2015/001104 filed on Mar. 3, 2015, which claims priority under 35 U.S.C. § 119(a) to Japanese Patent Application No. 2014-042495 filed on Mar. 5, 2014. Each of the above applications is hereby expressly incorporated by reference, in its entirety, into the present application.

BACKGROUND OF THE INVENTION

1. Field of the Invention

The present invention relates to a radiographic image processing device and a radiographic image processing method which perform a noise removal process for removing quantum noise included in a radiographic image and a program which causes a computer to perform a radiographic image processing method.

2. Description of the Related Art

In recent years, when diagnosis is performed using a radiographic image of a subject, image processing, such as a frequency enhancement process and a gradation process, has been performed for a captured radiographic image to change the radiographic image to an image suitable for diagnosis and the image has been displayed on a display device, such as a liquid crystal monitor, or has been output as a hard copy on a film. Here, a radiographic image has the problem that quantum noise of radiation is noticeable in a portion in which a radiation dose is small and density is low. Therefore, as image processing for a radiographic image, various methods have been proposed which perform a noise removal process for reducing or removing quantum noise included in a radiographic image.

For example, a smoothing process which uses a smoothing filter for removing a frequency component corresponding to quantum noise is known as the noise removal process. For example, JP2002-133410A discloses a method which performs frequency conversion for a radiographic image to create a band image indicating frequency components in different frequency bands, detects an edge direction of a pixel of interest to be processed in the band image, performs a smoothing process along the edge direction, performs frequency synthesis for the band image subjected to the smoothing process, and acquires a processed radiographic image. The use of the method disclosed in JP2002-133410A makes it possible to remove noise included in the radiographic image, without the deterioration of an edge component in the radiographic image.

During the capture of a radiographic image of a subject, when the thickness of the subject is too large, radiation is scattered in the subject and the contrast of the acquired radiographic image is reduced due to the scattered radiation (hereinafter, also referred to as scattered ray). As such, when a gradation process which enhances contrast or frequency processing which enhances a frequency component of an edge portion included in the subject is performed for the radiographic image of which the contrast has been reduced, it is possible to reduce the influence of scattered radiation and to obtain a high-quality radiographic image suitable for diagnosis.

SUMMARY OF THE INVENTION

Here, when radiation is scattered in the subject, the amount of radiation which reaches a radiation detector for detecting radiation passing through the subject is reduced. As a result, quantum noise of the radiographic image is noticeable. When the body thickness of the subject is too large, the amount of scattered radiation increases. As a result, quantum noise is noticeable in the radiographic image. Therefore, when contrast enhancement or frequency processing is performed in order to prevent a reduction in contrast caused by the scattered radiation, quantum noise included in the radiographic image is also enhanced. As a result, noise is noticeable and the quality of the radiographic image deteriorates.

The invention has been made in view of the above-mentioned problems and an object of the invention is to provide a technique which can effectively remove quantum noise included in a radiographic image, considering the body thickness of a subject.

As the body thickness of a subject increases, the amount of radiation scattered in the subject increases and the amount of quantum noise included in a radiographic image increases. The invention has been made in view of this problem. That is, a radiographic image processing device according to the invention comprises: image acquisition means for acquiring a radiographic image which is captured by irradiating a subject with radiation; body thickness information acquisition means for acquiring body thickness information indicating a body thickness of the subject; and noise removal means for removing noise included in the radiographic image on the basis of the body thickness information.

The "body thickness" means the total thickness of a subject region except for an air region on a path of the emitted radiation.

In the radiographic image processing device according to the invention, the noise removal means may increase a degree of removal of the noise as the body thickness of the subject based on the body thickness information increases.

In the radiographic image processing device according to the invention, the body thickness information acquisition means may analyze the radiographic image and acquire the body thickness information.

In the radiographic image processing device according to the invention, the body thickness information acquisition means may measure the body thickness of the subject and acquire the body thickness information.

In the radiographic image processing device according to the invention, the body thickness information acquisition means may receive an input body thickness of the subject and acquire the body thickness information.

In the radiographic image processing device according to the invention, the noise removal means may estimate an amount of noise included in the radiographic image on the basis of an amount of radiation emitted to the subject, convert the amount of noise on the basis of the body thickness information, and remove the noise in the radiographic image on the basis of the converted amount of noise.

In the radiographic image processing device according to the invention, the noise removal means may convert contrast of the radiographic image according to the body thickness information to acquire a converted radiographic image, calculate a difference between corresponding pixel positions of the converted radiographic image and the radiographic image, and convert the amount of noise according to the difference between the corresponding pixel positions, thereby converting the amount of noise on the basis of the body thickness information.

In the radiographic image processing device according to the invention, the noise removal means may calculate an average body thickness of the subject from the body thickness information and convert the amount of noise on the basis of the average body thickness.

In the radiographic image processing device according to the invention, the noise removal means may perform a filtering process for the radiographic image, using a smoothing filter corresponding to the converted amount of noise, to remove the noise in the radiographic image.

The radiographic image processing device according to the invention may further comprise input means for receiving input information for converting the amount of noise.

The radiographic image processing device according to the invention may further comprise image processing means for performing image processing that improves image quality for the radiographic image from which the noise has been removed.

A radiographic image processing method according to the invention comprises: acquiring a radiographic image which is captured by irradiating a subject with radiation; acquiring body thickness information indicating a body thickness of the subject; and removing noise included in the radiographic image on the basis of the body thickness information.

A program for causing a computer to perform the radiographic image processing method according to the invention may be provided.

According to the invention, noise included in the radiographic image is removed on the basis of the body thickness information indicating the body thickness of the subject. Therefore, it is possible to perform a noise removal process such that the degree of removal of noise increases as the body thickness of the subject increases, the amount of scattered radiation increases, and the amount of noise included in the radiographic image increases. It is possible to effectively remove noise from the radiographic image according to the body thickness of the subject. As a result, it is possible to acquire a high-quality radiographic image in which the amount of noise has been reduced.

In addition, the radiographic image is analyzed to acquire the body thickness information. Therefore, the body thickness information is acquired regardless of the operation of the operator and noise in the radiographic image is removed. As a result, it is possible to effectively remove noise in the radiographic image.

Furthermore, the body thickness of the subject is measured to acquire the body thickness information. Therefore, it is possible to easily acquire the body thickness information.

The input body thickness of the subject is received to acquire the body thickness information. Therefore, means for analyzing a radiographic image or means for measuring the body thickness is not required. As a result, it is possible to simplify the structure of a device.

BRIEF DESCRIPTION OF THE DRAWINGS

FIG. 5 is a flowchart illustrating a body thickness information acquisition process.

FIG. 6 is a diagram illustrating an example of an estimated image generation method.

DESCRIPTION OF THE PREFERRED EMBODIMENTS

Figure 1:
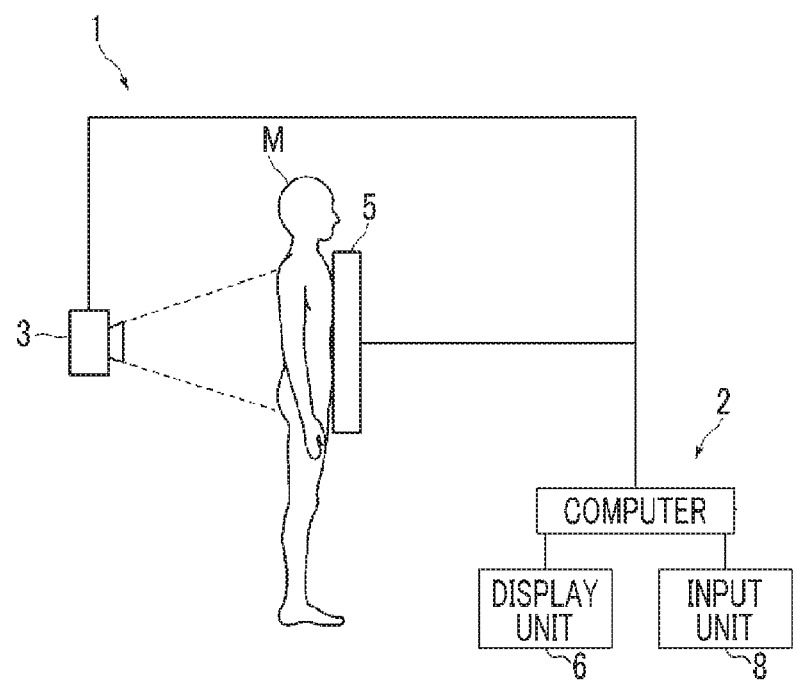
FIG. 1 is a block diagram schematically illustrating the structure of a radiography system to which a radiographic image processing device according to an embodiment of the invention is applied.

Hereinafter, embodiments of the invention will be described with reference to the drawings. FIG. 1 is a block diagram schematically illustrating the structure of a radiography system to which a radiographic image processing device according to an embodiment of the invention is applied. As illustrated in FIG. 1, the radiography system according to this embodiment performs various types of image processing including a noise removal process for removing quantum noise (hereinafter, simply referred to as noise) included in a radiographic image for a radiographic image of a subject. As illustrated in FIG. 1, the radiography system comprises an imaging device 1 and a computer 2 including the radiographic image processing device according to this embodiment.

The imaging device 1 comprises an X-ray source 3 which irradiates a subject M with X-rays and a radiation detector 5 which detects X-rays passing through the subject M and acquires a radiographic image of the subject M.

The radiation detector 5 can repeatedly perform a process of recording and reading a radiographic image and may be a so-called direct radiation detector which directly receives radiation and generates charge or a so-called indirect radiation detector which converts radiation into visible light and converts the visible light into a charge signal. In addition, as a method for reading a radiographic image signal, it is preferable to use a so-called thin film transistor (TFT) reading method which turns on and off a TFT switch to read a radiographic image signal or a so-called optical reading method which emits reading light to read a radiographic image signal. However, the invention is not limited thereto. Other methods may be used.

Figure 2:
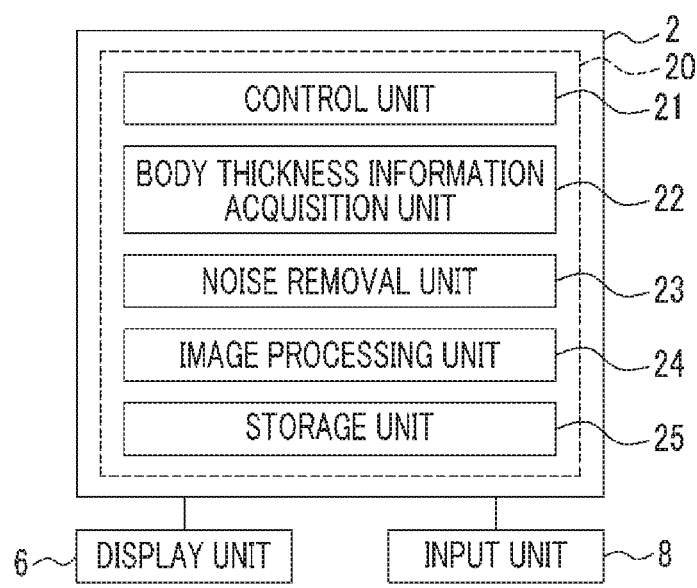
FIG. 2 is a block diagram schematically illustrating the internal structure of a computer of the radiography system according to this embodiment.

The computer 2 comprises, for example, a central processing unit (CPU), a semiconductor memory, a communication interface, and a storage device, such as a hard disk or an SSD. A control unit 21, a body thickness information acquisition unit 22, a noise removal unit 23, an image processing unit 24, and a storage unit 25 illustrated in FIG. 2 are implemented by these hardware components. The control unit 21, the body thickness information acquisition unit 22, the noise removal unit 23, the image processing unit 24, and the storage unit 25 form a radiographic image processing device 20 according to the invention.

The control unit 21 controls the capture of an image by the X-ray source 3 and the radiation detector 5, controls the reading of the radiographic image from the radiation detector 5, or controls all of the processes performed in the computer 2. The control unit 21 corresponds to image acquisition means according to the invention.

Figure 3:
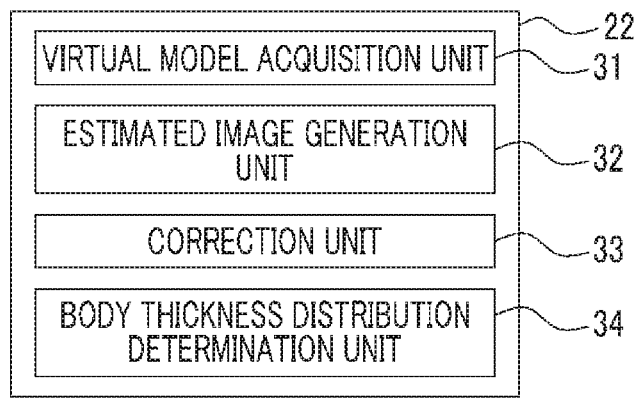
FIG. 3 is a block diagram schematically illustrating the structure of a body thickness information acquisition unit.

The body thickness information acquisition unit 22 estimates the body thickness of the subject M on the basis of the radiographic image and acquires the body thickness as body thickness information indicating the body thickness of the subject M. FIG. 3 is a block diagram schematically illustrating the structure of the body thickness information acquisition unit 22. As illustrated in FIG. 3, the body thickness information acquisition unit 22 comprises a virtual model acquisition unit 31, an estimated image generation unit 32, a correction unit 33, and a body thickness distribution determination unit 34. The body thickness means the total thickness of a subject region except for an air region on the path of the emitted radiation.

The virtual model acquisition unit 31 acquires a virtual model K of the subject M having an initial body thickness distribution T0 (predetermined body thickness distribution).

The estimated image generation unit 32 generates a composite image of an estimated primary radiation image Ip, which is obtained by estimating a primary radiation image obtained by radiography of the virtual model, and an estimated scattered radiation image Is, which is obtained by estimating a scattered radiation image obtained by radiography of the virtual model, as an estimated image Im which is obtained by estimating a radiographic image obtained by radiography of the subject M, on the basis of the virtual model K.

The correction unit 33 corrects the initial body thickness distribution T0 of the virtual model K such that the difference between the estimated image Im and the radiographic image is reduced, on the basis of the estimated image Im and the radiographic image.

The body thickness distribution determination unit 34 determines a corrected body thickness distribution Tn−1 (n is a natural number) to be a body thickness distribution Tk of the radiographic image.

The noise removal unit 23 performs a process that estimates the amount of noise included in the radiographic image on the basis of the amount of radiation which reaches the radiation detector 5, converts the estimated amount of noise on the basis of the body thickness information, and removes noise from the radiographic image on the basis of the converted amount of noise.

The image processing unit 24 performs various types of image processing for improving the quality of the radiographic image, which include a gradation process for adjusting contrast and frequency processing for enhancing the edge of the subject included in the radiographic image, for the radiographic image from which noise has been removed and generates a processed radiographic image.

The storage unit 25 stores various kinds of information such as a lookup table in which various body thicknesses, which will be described below, and the amount of conversion of noise are associated with each other.

The display unit 6 is, for example, a CRT display or a liquid crystal display and assists the display of a captured radiographic image and various inputs required for image processing which will be described below. The input unit 8 is, for example, a keyboard, a mouse, or a touch panel.

A central processing unit executes a computer program stored in the storage unit 25 to implement the processes performed by the control unit 21, the body thickness information acquisition unit 22, the noise removal unit 23, and the image processing unit 24. In addition, a plurality of processing devices which perform the processes of each unit may be provided in the computer 2.

Figure 4:
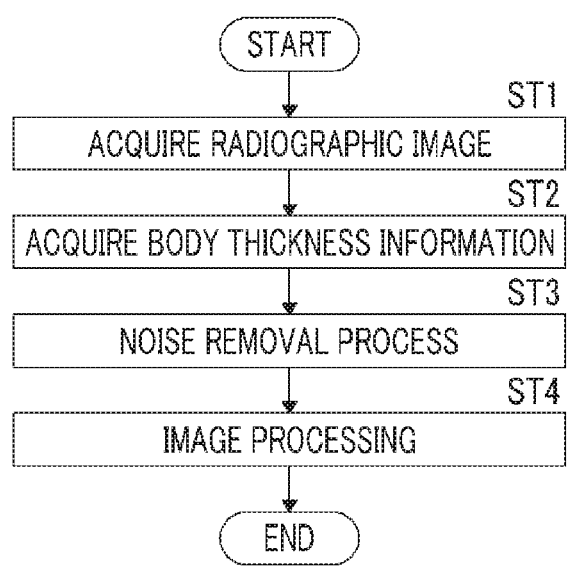
FIG. 4 is a flowchart illustrating a process performed in this embodiment.

Next, a process performed in this embodiment will be described. FIG. 4 is a flowchart illustrating the process performed in this embodiment. When a radiographic image of the subject M is captured and the control unit 21 of the computer 2 acquires the radiographic image (Step ST1), the body thickness information acquisition unit 22 estimates the body thickness of the subject M and acquires the estimated body thickness as body thickness information (Step ST2).

FIG. 5 is a flowchart illustrating a body thickness estimation process. The virtual model acquisition unit 31 of the body thickness information acquisition unit 22 acquires the virtual model K of the subject M having an initial body thickness distribution $T_0(x, y)$ (Step ST21). The virtual model K is data which virtually indicates the subject M and in which a body thickness that follows the initial body thickness distribution $T_0(x, y)$ is associated with each position on an x-y plane. In addition, structures (here, anatomic structures such as a lung field, a bone, and an organ) included in the virtual model K, the arrangement of the structures, and characteristic information indicating, for example, the characteristics of the structures with respect to radiation are set on the basis of the arrangement and composition of anatomic structures, such as the lung field of the chest and abdomen and the bones, in a subject model which has been created in advance.

The virtual model K which is created in advance so as to have an arbitrary initial body thickness distribution $T_0(x, y)$ and is then stored in the storage unit 25 may be used. In this embodiment, the initial body thickness distribution T0 is generated and acquired by the virtual model acquisition unit 31. The virtual model acquisition unit 31 acquires imaging conditions, such as the amount of radiation (radiation dose) emitted to the subject M, a tube voltage, and an SID, and acquires a lookup table (hereinafter, referred to as LUT0) in which a pixel value corresponding to the imaging conditions of the subject M is associated with the body thickness from the storage unit 25. Then, the virtual model acquisition unit 31 specifies the body thickness corresponding to the value of each pixel in the radiographic image of the subject M on the basis of the LUT0 to acquire the body thickness distribution of the radiographic image. Then, the virtual model acquisition unit 31 acquires the body thickness distribution of the radiographic image as the initial body thickness distribution T0 (predetermined body thickness distribution) of the virtual model K. The initial body thickness distribution T0 may be generated during the process of acquiring the virtual model K as in this embodiment, or may be set in advance before the process of acquiring the virtual model K. The above-mentioned process is represented by the following Expression (1). In addition, I(x, y) indicates the value of each pixel in a radiographic image and $T_0(x, y)$ indicates an initial body thickness distribution at each pixel position.

$$T_0(x,y) = \text{LUT}(I(x,y)) \qquad (1)$$

Figure 7:
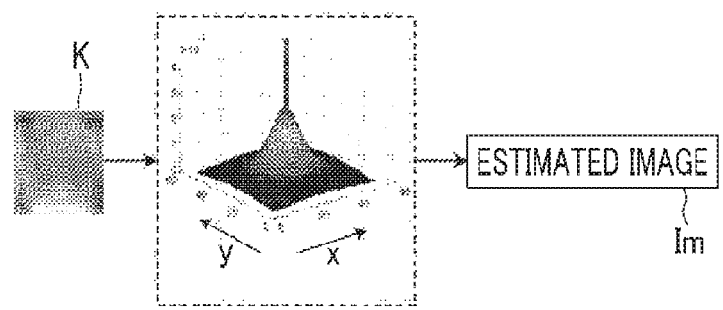
FIG. 7 is a diagram illustrating another example of the estimated image generation method.

Then, the estimated image generation unit 32 combines an estimated primary radiation image Ip, which is obtained in a case in which the image of the virtual model K is captured under the same imaging conditions as the radiographic image, and an estimated scattered radiation image Is, which is obtained in a case in which the image of the virtual model K is captured under the same imaging conditions as the radiographic image, to generate an estimated image Im (Step ST22). FIGS. 6 and 7 are diagrams illustrating a method for generating the estimated image Im.

As illustrated in FIG. 6, the estimated image generation unit 32 generates the estimated primary radiation image Ip, which is obtained in a case in which the image of the virtual model K is captured under the same imaging conditions as the radiographic image, according to the following Expression (2), and generates the estimated scattered radiation image Is, using the generated estimated primary radiation image Ip, according to the following Expression (3). Then, the estimated image generation unit 32 combines the estimated primary radiation image Ip and the estimated scattered radiation image Is to generate the estimated image Im, as shown in the following Expression (4) (Step ST22). When the estimated primary radiation image Ip and the estimated scattered radiation image Is are generated first, the initial body thickness distribution $T_0(x, y)$ is used in Estimation Expressions (2) and (3) (n is 1 in Expressions (2) and (3)).

$$I_p(x, y) = I_o(x, y) \times \exp(-T_{n-1}(x, y) \times \mu) \quad (2)$$

$$I_s(x, y) = \sum_{x',y'} I_p(x', y') K_s(x, y, T_{n-1}(x', y'), \theta_{x',y'}) \quad (3)$$

$$I_m(x, y) = I_p(x, y) + I_s(x, y) \quad (4)$$

Here, (x, y) is the coordinates of a pixel position in a radiographic image, Ip(x, y) is an estimated primary radiation image at the pixel position (x, y), Is(x, y) is an estimated scattered radiation image at the pixel position (x, y), Io(x, y) is a dose at the pixel position (x, y), Im(x, y) is an estimated image at the pixel position (x, y), μ is a linear attenuation coefficient of the subject, and Ks(x, y, Tn(x', y'), θx', y') is a convolution kernel indicating a point spread function corresponding to the thickness of the subject at the pixel position (x, y). The dose Io(x, y) is a radiation dose which is detected by the radiation detector 5 on the assumption that no subject is present and varies depending on the distance (SID) between the X-ray source 3 and a detection surface of the radiation detector 5, a tube voltage, and an mAs value. In addition, θx', y' indicates a parameter which is specified by the imaging conditions, such as the tube voltage, or the characteristic information of the virtual model K.

In addition, the estimated image Im may be an image which is estimated to be obtained in a case in which the radiographic image of the virtual model K is captured and may be any image which is substantially regarded as a composite image of the estimated primary radiation image Ip and the estimated scattered radiation image Is. For example, as illustrated in FIG. 7, the estimated image Im may be generated by the convolution integral of the kernel combining a primary radiation component and a scattered component, using the following Expression (5), instead of Expressions (2) to (4). Here, Kp+s(x, y, Tn-1(x', y'), θx', y') is a kernel indicating a point spread function that combines the primary radiation component and the scattered component. In addition, any model function may be used as long as it can generate an estimated image obtained by combining the estimated primary radiation image and the estimated scattered radiation image from the image obtained by radiography.

In addition, Ks(x, y, Tn(x', y'), θx', y') and Kp+s(x, y, Tn-1(x', y'), θx', y') can be experimentally calculated according to, for example, imaging conditions.

In this embodiment, the kernels Ks(x, y, Tn(x', y'), θx', y') and Kp+s(x, y, Tn-1(x', y'), θx', y') may be calculated on the basis of the imaging conditions during imaging. An LUT in which various imaging conditions and the kernels Ks(x, y, Tn(x', y'), θx', y') and Kp+s(x, y, Tn-1(x', y'), θx', y') are associated with each other is stored in the storage unit 25 and the kernels Ks(x, y, Tn(x', y'), θx', y') and Kp+s(x, y, Tn-1(x', y'), θx', y') are calculated on the basis of irradiation field information, subject information, and imaging conditions during imaging, with reference to the LUT.

$$I_m(x, y) = \sum_{x',y'} K_{p+s}(x, y, T_{n-1}(x', y'), \theta_{x',y'}) \quad (5)$$

The next process will be described with reference to the flowchart illustrated in FIG. 5. Then, the body thickness distribution determination unit 34 determines whether the difference between the radiographic image and the estimated image Im satisfies end conditions (Step ST23). Here, the following error value $V_{error}$ indicating the difference between the radiographic image and the estimated image Im is defined as shown in Expressions (6) and (7). It is determined whether the error value $V_{error}$ is equal to or less than a threshold value as the end conditions. As shown in Expression (7), the sum of the squares of each pixel value of a difference image Id which is obtained by subtracting the estimated image Im from the radiographic image is defined as an error function $f_{error}$. In addition, any determination method may be used as long as it can determine whether or not the difference between the radiographic image and the estimated image Im is small enough to be allowable, as the end conditions.

$$V_{error} = f_{error}(I_m(x, y), I(x, y)) \quad (6)$$

$$f_{error}(I_m(x, y), I(x, y)) = \sum_{x,y} (I_m(x, y) - I(x, y))^2 \quad (7)$$

However, the invention is not limited to the above-mentioned example. For example, the error function $f_{error}$ can be defined by any method which can indicate the difference between the radiographic image and the estimated image Im. For example, as shown in the following Expression (8), the sum of the absolute values of each pixel value of the differential image Id obtained by subtracting the estimated image Im from the radiographic image may be defined as the error function $f_{error}$.

$$f_{error}(I_m(x, y), I(x, y)) = \sum_{x,y} |I_m(x, y) - I(x, y)| \quad (8)$$

In a case in which the error value $V_{error}$ does not satisfy the end conditions (Step ST23; No), the body thickness distribution determination unit 34 performs a correction process of correcting the body thickness distribution Tn-1 (the initial body thickness distribution T0 in a case in which n is 1) (Step ST24).

Any method which can acquire a correction value of each position in the body thickness distribution Tn-1 such that the difference between the radiographic image and the estimated image Im is reduced can be applied in order to perform the process of correcting the body thickness distribution Tn−1. In this embodiment, a process is performed which changes the body thickness distribution Tn−1 of the virtual model K for each partial region including one or more pixels in the virtual model K to calculate the body thickness of the partial region where the difference between the estimated image Im and the radiographic image is small. Then, the body thickness distribution of the virtual model is corrected using the calculated body thickness of each partial region.

Specifically, in this embodiment, it is assumed that the correction value of the body thickness with the body thickness distribution Tn−1 is calculated using the steepest descent method. It is possible to minimize the output value of the error function $f_{error}$ by repeatedly calculating dTn−1 (x, y) on the basis of the primary partial differential (gradient) of the error function $f_{error}$ while changing only the body thickness at one specific coordinate point in Tn−1(x, y) among the pixels of the virtual model K, using the following Expressions (9) and (10). Then, the body thickness at one specific coordinate point when the output value of the error function $f_{error}$ is minimized is determined as the correction value of the body thickness at the specific coordinate point. For the other pixels, similarly, the correction value of each body thickness is calculated and the body thickness distribution of each pixel is corrected. In this way, a corrected body thickness distribution Tn is acquired.

$$T_n(x, y) = T_{n-1}(x, y) - \alpha dT_{n-1}(x, y) \quad (9)$$
$$= T_{n-1}(x, y) - \alpha \frac{d}{dT_{n-1}(x, y)} f_{error}$$

$$\frac{d}{dT_{n-1}(x, y)} f_{error} = \quad (10)$$
$$\sum_{x',y'} (I_m(x', y') - I(x', y')) \frac{d}{dT_{n-1}(x, y)} K_{p+s}(x', y', T_{n-1}(x, y), \theta_{x,y})$$

$$\frac{d}{dT_{n-1}(x, y)} K_{p+s}(x', y', T_{n-1}(x, y), \theta_{x,y}) = \quad (11)$$
$$K_{p+s}(x', y', T_{n-1}(x, y) + dt, \theta_{x,y}) - K_{p+s}(x', y', T_{n-1}(x, y), \theta_{x,y})$$

However, in Expression (9), α is an update coefficient which is a parameter indicating the update speed of the body thickness. As an example of a method for calculating a differential value portion of Kp+s shown in Expression (10), for example, a value change when a very small value dt is added to Tn−1(x, y) can be calculated by Expression (11) and can be used as the value of Kp+s in the Expression (10). In Expressions (1) to (11), the same components are denoted by the same reference numerals and the description thereof will not be repeated. Any optimization method can be applied as long as it can minimize the error value $V_{error}$ indicating the difference between the radiographic image and the estimated image Im. For example, a simplex method, the steepest descent method, or a conjugate gradient method can be used.

When the corrected body thickness distribution Tn is acquired, the body thickness distribution determination unit 34 increases the value of n by 1 to update the value of n (n=n+1) and the virtual model acquisition unit 31 acquires the corrected body thickness distribution Tn (Step ST21). Then, the estimated image generation unit 32 and the body thickness distribution determination unit 34 perform the process from Step ST21 to Step ST23 for the acquired body thickness distribution Tn, using the same method as described above. Then, similarly, the process of correcting the body thickness distribution Tn (Step ST24), the process of acquiring the virtual model K having the corrected body thickness distribution Tn (Step ST21), the process of generating a new estimated image Im using the body thickness distribution Tn (Step ST22), and the process of determining whether the difference between a newly generated estimated image Im and the radiographic image satisfies the end conditions (Step ST23) are repeatedly performed until the error value $V_{error}$ indicating the difference between the radiographic image and the estimated image Im satisfies the end conditions.

On the other hand, in a case in which it is determined that the error value $V_{error}$ satisfies the end conditions (Step ST23: Yes), the body thickness distribution determination unit 34 determines the body thickness distribution Tn which is used for the error value $V_{error}$ when the end conditions are satisfied as the body thickness distribution Tk of the radiographic image, outputs the body thickness distribution Tn as body thickness information, and ends a body thickness information acquisition process (Step ST25).

Figure 8:
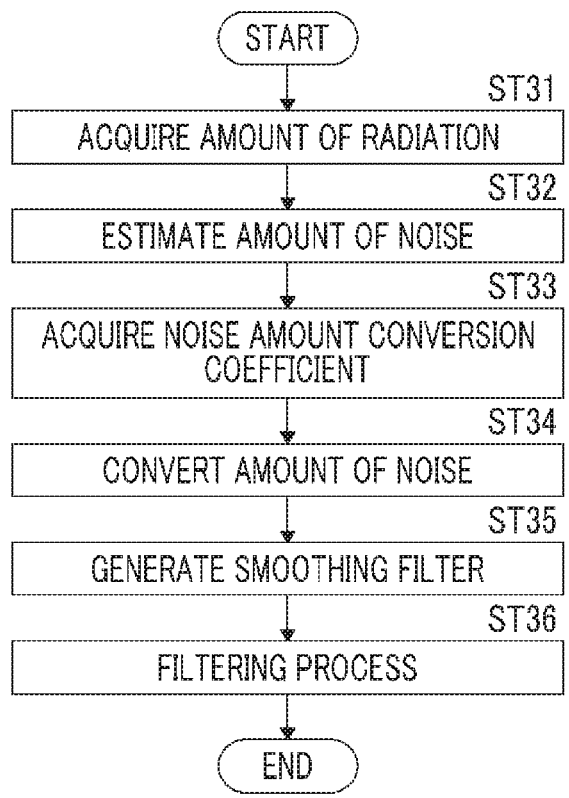
FIG. 8 is a flowchart illustrating a noise removal process.

Returning to FIG. 4, following the body thickness information acquisition process, the noise removal unit 23 performs a process of removing noise from the radiographic image on the basis of the body thickness information (Step ST3). FIG. 8 is a flowchart illustrating the noise removal process. First, the noise removal unit 23 acquires information about the amount of radiation during imaging (Step ST31). The dose Io(x, y) which is used by the body thickness information acquisition unit 22 to acquire the body thickness information may be used as the information about the amount of radiation. Then, the amount of quantum noise included in the radiographic image is estimated with reference to a lookup table (which is referred to as LUT1) in which the amount of radiation and noise are associated with each other and which is stored in the storage unit 25 (Step ST32).

Figure 9:
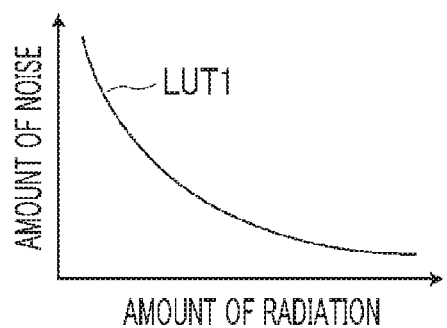
FIG. 9 is a diagram illustrating a lookup table in which the amount of radiation is associated with noise.

FIG. 9 is a diagram illustrating the lookup table in which the amount of radiation and noise are associated with each other. As illustrated in FIG. 9, the LUT1 is a lookup table in which the amount of noise increases as the amount of radiation decreases and the amount of noise decreases non-linearly as the amount of radiation increases. In addition, the LUT1 is generated by a simulation which measures the amount of noise included in the radiographic image in a case in which the subject M having a predetermined body thickness is irradiated with various radiation doses. The noise removal unit 23 estimates the amount of noise included in the radiographic image from the amount of radiation, with reference to the LUT1.

Figure 10:
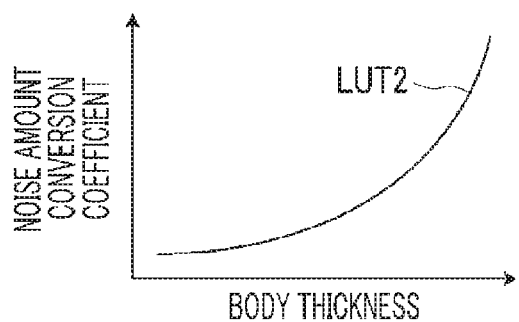
FIG. 10 is a diagram illustrating a lookup table in which a body thickness is associated with a noise amount conversion coefficient.

Then, the noise removal unit 23 acquires a noise amount conversion coefficient for converting the estimated amount of noise, on the basis of the body thickness information acquired by the body thickness information acquisition unit 22 (Step ST33). The noise amount conversion coefficient is acquired with reference to a lookup table (which is referred to as LUT2) in which the body thickness and the noise amount conversion coefficient are associated with each other and which is stored in the storage unit 25. FIG. 10 is a diagram illustrating a lookup table in which the body thickness and the amount noise conversion coefficient are associated with each other. As illustrated in FIG. 10, the LUT2 is a lookup table in which the noise amount conversion coefficient decreases as the body thickness decreases and the noise amount conversion coefficient increases non-linearly as the body thickness increases.

The LUT1 illustrated in FIG. 9 is created by a simulation using a subject having a predetermined body thickness.

Therefore, in the LUT2 illustrated in FIG. 10, when the body thickness is the body thickness of the subject which is used to create the LUT1, the noise amount conversion coefficient which is obtained with reference to the LUTZ is 1.0. The noise removal unit 23 acquires the noise amount conversion coefficient from the body thickness information with reference to the LUT2. In the case of the body thickness used to create the LUT1, the noise amount conversion coefficient is 0 and a lookup table may be created such that the noise amount conversion coefficient increases as the body thickness increases and the noise conversion coefficient becomes a smaller negative value as the body thickness becomes smaller. In this case, the lookup table is referred to as LUT3.

Then, the noise removal unit 23 converts the amount of noise using the noise amount conversion coefficient (Step ST34). The amount of noise is converted by multiplying the estimated amount of noise by the noise amount conversion coefficient. In a case in which the LUT3 is used, the amount of noise may be converted by adding the noise amount conversion coefficient to the estimated amount of noise.

Figure 11:
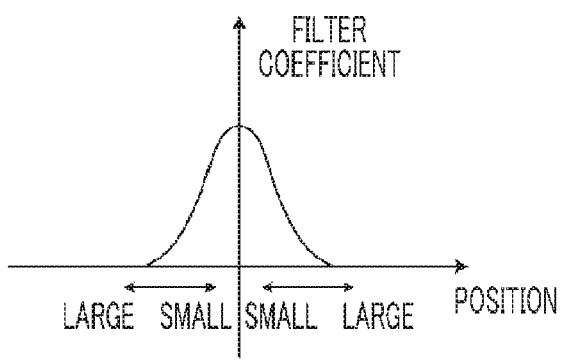
FIG. 11 is a diagram illustrating a smoothing filter.

Then, the noise removal unit 23 creates a smoothing filter for removing noise from the radiographic image, using the converted amount of noise (Step ST35). FIG. 11 is a diagram illustrating the creation of the smoothing filter. The smoothing filter is a two-dimensional filter. However, here, for convenience of explanation, the smoothing filter is one-dimensionally illustrated. As illustrated in FIG. 11, the smoothing filter is a Gaussian filter. The smoothing filter is created such that a filter size (that is, a size in the horizontal axis direction in FIG. 11) increases as the amount of noise increases.

Then, the noise removal unit 23 performs a filtering process for the radiographic image using the smoothing filter to generate a radiographic image from which noise has been removed and ends the noise removal process (Step ST36).

Returning to FIG. 4, following the noise removal process, the image processing unit 24 performs image processing for improving image quality, such as a contrast enhancement process and frequency processing, for the radiographic image from which noise has been removed (Step ST4) and ends the process. The amount of scattered radiation by the subject M increases as the body thickness of the subject M increases and the contrast of the radiographic image is reduced. Therefore, the image processing unit 24 performs a gradation process, using the body thickness information acquired by the body thickness information acquisition unit 22, such that the degree of enhancement of the contrast increases as the body thickness increases. In addition, the image processing unit 24 performs frequency processing such that the degree of enhancement of an edge component of the subject M increases as the body thickness increases. The processed radiographic image is displayed on the display unit 6 or is stored in a database (not illustrated).

As such, in this embodiment, noise included in a radiographic image is removed on the basis of body thickness information indicating the body thickness of a subject. Specifically, as the body thickness of the subject increases, the amount of scattered radiation increases. The noise removal process is performed such that, as the amount of noise included in the radiographic image increases, the degree of removal of noise increases. Therefore, it is possible to effectively remove noise from the radiographic image according to the body thickness of the subject. As a result, it is possible to acquire a high-quality radiographic image with a reduced amount of noise. In addition, even if a gradation process for contrast enhancement is performed, noise is not noticeable. Therefore, it is possible to acquire a high-quality radiographic image suitable for diagnosis.

In addition, the radiographic image is analyzed to acquire the body thickness information. Therefore, if the operator does not perform any operation, the body thickness information is acquired and noise is removed from the radiographic image. Therefore, it is possible to effectively remove noise from the radiographic image.

Figure 12:
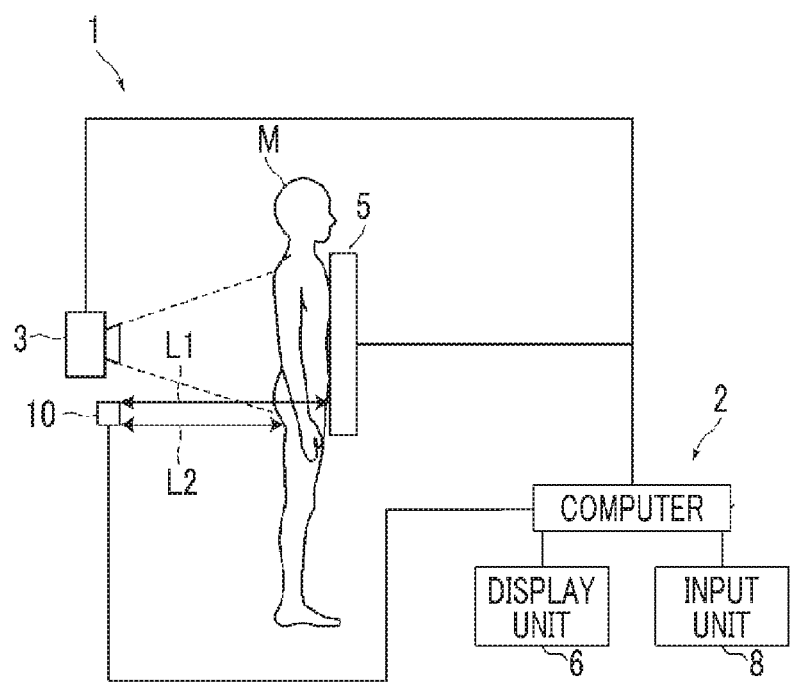
FIG. 12 is a block diagram schematically illustrating the structure of a radiography system comprising a body thickness measurement device.

In the above-described embodiment, the body thickness information acquisition unit 22 analyzes the radiographic image to acquire the body thickness information of the subject M. As illustrated in FIG. 12, a distance measurement device 10, such as an ultrasonic range finder, may be provided in the imaging device 1, may measure a distance L1 between the X-ray source 3 and the detection surface of the radiation detector 5 and a distance L2 between the X-ray source 3 and the surface of the subject M, and may input the measurement result to the computer 2. The body thickness information acquisition unit 22 may calculate the difference between the distance L1 and the distance L2 and acquire body thickness information. In this case, it is not necessary to analyze the radiographic image. Therefore, it is possible to easily acquire the body thickness information.

In addition, the operator may measure the body thickness of the subject M and input the measurement result to the computer 2 through the input unit 8. In this case, the body thickness information acquisition unit 22 may acquire the body thickness input from the input unit 8 as the body thickness information, without any change. In this case, it is not necessary to provide a device for analyzing the radiographic image or a device for measuring the body thickness. Therefore, it is possible to simplify the structure of the radiography system to which the radiographic image processing device according to the invention is applied.

In the above-described embodiment, the body thickness information at each pixel position (x, y) of the radiographic image is acquired. However, the average value of the body thickness which is estimated using the radiographic image may be used as the body thickness information.

Figure 13:
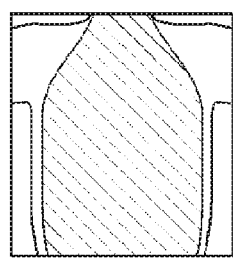
FIG. 13 is a diagram illustrating a distribution of an absolute value of a difference value between a radiographic image and a radiographic image subjected to a gradation process.

In the above-described embodiment, the noise amount conversion coefficient is calculated from the body thickness information with reference to the LUT2. However, the image processing unit 24 may perform a gradation process for the radiographic image, using the body thickness information, may calculate the absolute value of a difference value between the corresponding pixel positions of the radiographic image subjected to the gradation process and the original radiographic image before the gradation process, and may calculate the noise amount conversion coefficient on the basis of the absolute value of the difference value. Here, as the body thickness of the subject M increases, the amount of radiation scattered by the subject M increases and the contrast of the radiographic image is reduced. Therefore, the degree of contrast enhancement for a pixel corresponding to a larger body thickness in the radiographic image becomes larger. As a result, the absolute value of the difference value between a radiographic image and a radiographic image subjected to the gradation process increases. Therefore, as illustrated in FIG. 13, a distribution of the difference value in the radiographic image is obtained. In FIG. 13, the absolute value of the difference value is large in a hatched portion. The noise removal unit 23 may generate an LUT in which a noise amount conversion coefficient based on the absolute value of the difference value is associated with the body thickness information and acquire the noise conversion coefficient using the LUT. In addition, the absolute value of the difference value may be used as the noise amount conversion coefficient, without any change.

In the above-described embodiment, the filtering process using the smoothing filter is performed for the radiographic image to perform the noise removal process. However, as described in JP2002-133410A, a method may be used which performs frequency conversion for a radiographic image, creates a band image indicating frequency components in different frequency bands, detects the edge direction of a pixel of interest to be processed in the band image, performs a smoothing process along the edge direction, performs inverse frequency conversion for the band image subjected to the smoothing process, and acquires a processed radiographic image. In addition, known methods other than the above-mentioned method may be used.

In the above-described embodiment, the amount of noise is estimated from the information about the amount of radiation included in the imaging conditions. However, the amount of radiation which reaches the radiation detector 5 may be estimated from the reading sensitivity (S value) or the L value (latitude) of the radiation detector 5 and the amount of noise may be estimated on the basis of the estimated amount of radiation.

In the above-described embodiment, when the conversion of the amount of noise based on the body thickness information fails, noise is noticeable in the processed radiographic image displayed on the display unit 6. Therefore, in a case in which noise is noticeable when the processed radiographic image is displayed on the display unit 6, the radiographic image processing device may be configured such that the operator can input the noise amount conversion coefficient through the input unit 8 and the noise removal process is performed again, using the noise amount conversion coefficient input by the operator. In this case, in a case in which noise is noticeable in the processed radiographic image, it is possible to perform the noise removal process such that noise is reduced.

In the above-described embodiment, the scattered radiation removal process is performed for the radiographic image captured by the radiation detector 5. However, the invention can also be applied to the case disclosed in JP1996-266529A (JP-H08-266529A) and JP1997-24039A (JP-H09-24039A) in which the radiographic image information of the subject is stored and recorded on a storage phosphor sheet as a radiation detector and a radiographic image is photoelectrically read and acquired from the storage phosphor sheet and is then used.

What is claimed is:

1. A radiographic image processing device comprising:
   a memory configured to store executable instructions; and
   a processor configured to execute the executable instructions, which when executed by the processor cause the processor to perform the following functions:
   acquire a radiographic image which is captured by irradiating a subject with radiation;
   acquire body thickness information indicating a body thickness of the subject; and
   remove noise included in the radiographic image on the basis of the body thickness information by:
   estimating an amount of noise included in the radiographic image on the basis of an amount of radiation emitted to the subject,
   converting the amount of noise on the basis of the body thickness information, and
   removing the noise in the radiographic image on the basis of the converted amount of noise,
   wherein the processor further functions to convert contrast of the radiographic image according to the body thickness information to acquire a convert radiographic image, calculate a difference between corresponding pixel positions of the converted radiographic image and the radiographic image, and convert the amount of noise according to the difference between the corresponding pixel positions, thereby converting the amount of noise on the basis of the body thickness information, and
   wherein the removal of noise increases a degree of removal of the noise as the body thickness of the subject based on the body thickness information increases.

2. The radiographic image processing device according to claim 1,
   wherein the processor further functions to analyze the radiographic image and acquire the body thickness information.

3. The radiographic image processing device according to claim 1,
   wherein the processor further functions to measure the body thickness of the subject and acquire the body thickness information.

4. The radiographic image processing device according to claim 1,
   wherein the processor further functions to receive an input body thickness of the subject and acquire the body thickness information.

5. The radiographic image processing device according to claim 1,
   wherein the processor further functions to calculate an average body thickness of the subject from the body thickness information and convert the amount of noise on the basis of the average body thickness.

6. The radiographic image processing device according to claim 1,
   wherein the processor further functions to perform a filtering process for the radiographic image, using a smoothing filter corresponding to the converted amount of noise, to remove the noise in the radiographic image.

7. The radiographic image processing device according to claim 1, further comprising:
   an input unit for receiving input information for converting the amount of noise.

8. The radiographic image processing device according to claim 1, wherein the processor further functions to perform image processing that improves image quality for the radiographic image from which the noise has been removed.

9. A radiographic image processing method comprising:
   acquiring a radiographic image which is captured by irradiating a subject with radiation;
   acquiring body thickness information indicating a body thickness of the subject;
   and removing noise included in the radiographic image on the basis of the body thickness information by:
   estimating an amount of noise included in the radiographic image on the basis of an amount of radiation emitted to the subject,
   converting the amount of noise on the basis of the body thickness information,
   removing the noise in the radiographic image on the basis of the converted amount of noise,
   acquiring a converted radiographic image by converting contrast of the radiographic image according to the body thickness information, calculating a difference between corresponding pixel positions of the converted radiographic image and the radiographic image, and converting the amount of noise according to the difference between the corresponding pixel positions, thereby converting the amount of noise on the basis of the body thickness information, wherein removing the noise increases a degree of removal of the noise as the body thickness of the subject based on the body thickness information increases.

10. A non-transitory recording medium having a radiographic image processing program recorded therein, the radiographic image processing program causing a computer to perform:

a step of acquiring a radiographic image which is captured by irradiating a subject with radiation;

a step of acquiring body thickness information indicating a body thickness of the subject; and a step of removing noise included in the radiographic image on the basis of the body thickness information by:

estimating an amount of noise included in the radiographic image on the basis of an amount of radiation emitted to the subject, converting the amount of noise on the basis of the body thickness information, and removing the noise in the radiographic image on the basis of the converted amount of noise, a step of acquiring a converted radiographic image by converting contrast of the radiographic image according to the body thickness information, a step of calculating a difference between corresponding pixel positions of the converted radiographic Image and the radiographic image, and a step of converting the amount of noise according to the difference between the corresponding pixel positions, thereby converting the amount of noise on the basis of the body thickness information, wherein in the step of removing the noise, the removal of noise increases a degree of removal of the noise as the body thickness of the subject based on the body thickness information increases.

* * * * *